United States Patent [19]

Karanewsky et al.

[11] 4,444,765
[45] Apr. 24, 1984

[54] AMINO AND SUBSTITUTED AMINO PHOSPHINYLALKANOYL COMPOUNDS USEFUL FOR TREATING HYPERTENSION

[75] Inventors: Donald S. Karanewsky, Princeton Junction; Edward W. Petrillo, Jr., Pennington, both of N.J.

[73] Assignee: E. R. Squibb & Sons, Inc., Princeton, N.J.

[21] Appl. No.: 398,052

[22] Filed: Jul. 14, 1982

[51] Int. Cl.³ .................... A61K 31/675; C07F 9/65
[52] U.S. Cl. .................................. 424/200; 546/22; 546/23; 548/112; 548/119; 548/409; 548/413; 548/414
[58] Field of Search ............... 548/409, 413, 414, 112, 548/119; 546/22, 23; 424/200

[56] References Cited

U.S. PATENT DOCUMENTS 4,303,583 12/1981 Kim et al. ................. 424/200 X
4,337,201 6/1982 Petrillo, Jr. ................. 548/413
4,374,131 2/1983 Petrillo, Jr. ................. 424/200
4,381,297 4/1983 Karanewsky et al. ....... 424/200

Primary Examiner—Donald G. Daus
Assistant Examiner—Diana G. Rivers
Attorney, Agent, or Firm—Lawrence S. Levinson; Burton Rodney

[57] ABSTRACT

Compounds of the formula

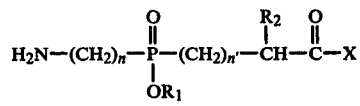

wherein X is an amino acid or ester are useful hypotensive agents due to their angiotensin converting enzyme inhibition activity.

13 Claims, No Drawings

AMINO AND SUBSTITUTED AMINO PHOSPHINYLALKANOYL COMPOUNDS USEFUL FOR TREATING HYPERTENSION

BACKGROUND OF THE INVENTION

Petrillo in U.S. Pat. No. 4,168,267 discloses that various phosphinylalkanoyl substituted prolines are useful as hypotensive agents due to their ability to inhibit the angiotensin converting enzyme.

Ondetti et al in U.S. Pat. No. 4,151,172 discloses that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti et al in U.S. Pat. No. 4,105,776 disclose such compounds wherein the proline ring is unsubstituted or substituted by an alkyl or hydroxy group. Ondetti et al in U.S. Pat. No. 4,154,935 disclose such compounds wherein the proline ring is substituted with one or more halogens. Ondetti et al in U.K. Patent Application No. 2,028,327 disclose such compounds wherein the proline ring is substituted by various ethers and thioethers. Krapcho in U.S. Pat. No. 4,217,359 discloses such compounds wherein the proline ring has a carbamoyloxy substituent. Krapcho in U.K. Patent Application No. 2,039,478 discloses such compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti et al in U.S. Pat. No. 4,234,489 disclose such compounds wherein the proline has a keto substituent in the 5-position. Krapcho et al in U.S. Pat. No. 4,310,461 disclose such compounds wherein the proline has an imido, amido, or amino substitutent in the 4-position. Iwao et al in U.K. Patent Application No. 2,027,025 disclose such compounds wherein the proline has an aromatic substituent in the 5-position.

Mercaptoacyl derivatives of 3,4-dehydroproline are disclosed as angiotensin converting emzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Pat. No. 868,532.

RELATED APPLICATIONS

Petrillo in U.S. application Ser. No. 258,194, now U.S. Pat. No. 4,374,131, discloses amino and substituted amino phosphinylalkanoyl compounds which include a methylene function linking an amino function and a phosphinyl function.

SUMMARY OF THE INVENTION

This invention is directed to new amino and substituted amino phosphinylalkanoyl compounds of formula I and salts thereof

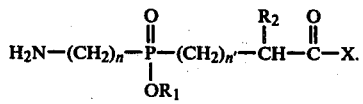

where
X is an imino acid of the formula

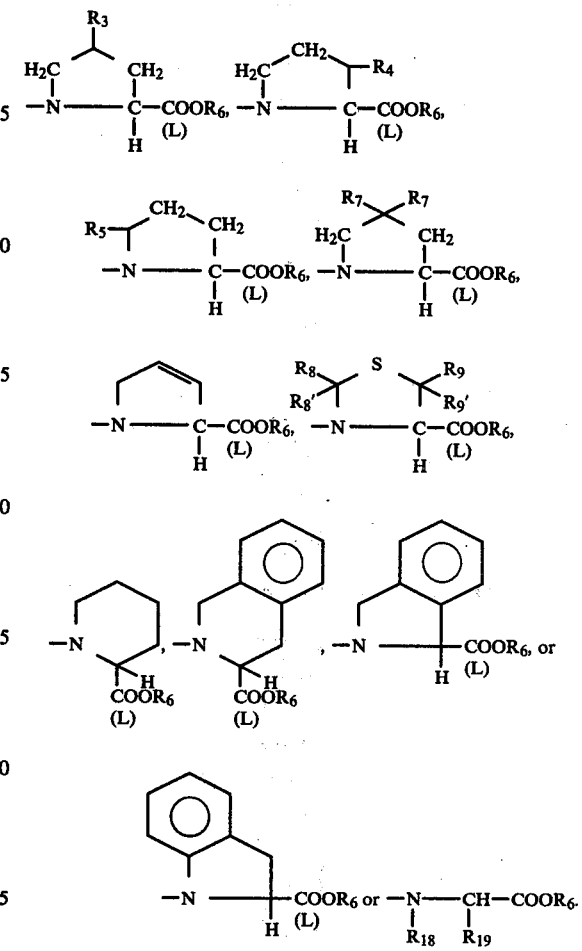

$R_3$ is hydrogen, lower alkyl, halogen, keto, hydroxy, $$-NH-\overset{O}{\underset{\|}{C}}-\text{lower}$$

alkyl, azido, $$-NH-\overset{O}{\underset{\|}{C}}-(CH_2)_m-\underset{(R_{11})_{p'}}{\phantom{x}}$$

$$-(CH_2)_m-\underset{(R_{10})_p}{\phantom{x}}, -(CH_2)_m-\underset{O}{\phantom{x}},$$

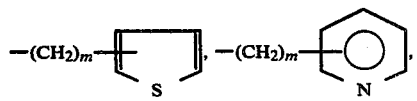

a 1- or 2-naphthyl of the formula

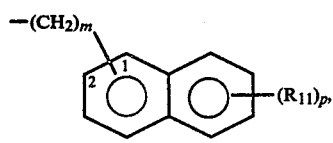

—(CH₂)ₘ—cycloalkyl,

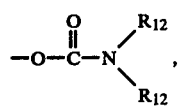

amino,

—O—lower alkyl,

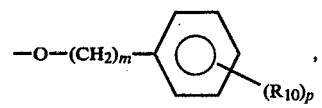

a 1- or 2-naphthyloxy of the formula

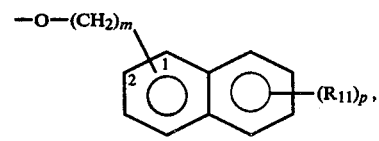

—S—lower alkyl,

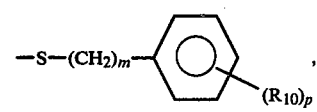

or a 1- or 2-naphthylthio of the formula

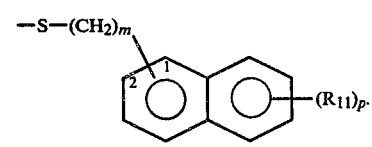

$R_4$ is keto, halogen,

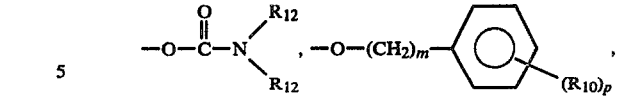

—O—lower alkyl, a 1- or 2-naphthyloxy of the formula

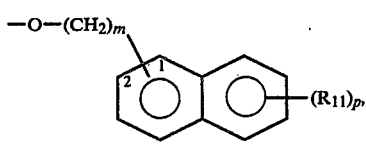

—S—lower alkyl,

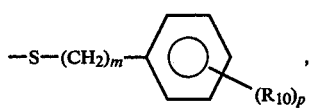

or a 1- or 2-naphthylthio of the formula

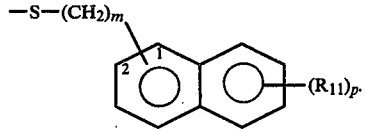

$R_5$ is keto or

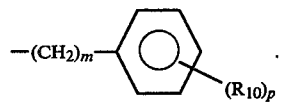

$R_7$ is halogen or Y-$R_{13}$.

$R_8$, $R_8'$, $R_9$ and $R_9'$ are independently selected from hydrogen and lower alkyl or $R_8'$, or $R_9$ and $R_9'$ are hydrogen and

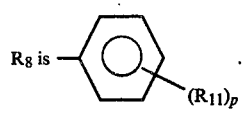

$R_{10}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two or three.

p is one, two or three provided that p is more than one only if $R_{10}$ or $R_{11}$ is hydrogen, methyl, methoxy, chloro, or fluoro.

$R_{12}$ is hydrogen or lower alkyl of 1 to 4 carbons.

Y is oxygen or sulfur.

$R_{13}$ is lower alkyl of 1 to 4 carbons,

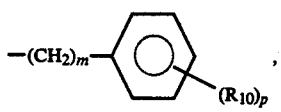

or the $R_{13}$ groups join to complete an unsubstituted 5- or 6-membered ring or said ring in which one or more of the carbons has a lower alkyl of 1 to 4 carbons or a di(lower alkyl of 1 to 4 carbons) substituent.

n is 4 to 8.

n' is 0 or 1.

$R_2$ is hydrogen, lower alkyl, halo substituted lower alkyl, benzyl or phenethyl.

$R_1$ and $R_6$ are independently selected from hydrogen, lower alkyl, benzyl, benzhydryl, or

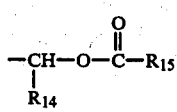

wherein $R_{14}$ is hydrogen, lower alkyl, cycloalkyl, or phenyl, and $R_{15}$ is hydrogen, lower alkyl, lower alkoxy, phenyl, or $R_{14}$ and $R_{15}$ taken together are $-(CH_2)_2-$, $-(CH_2)_3-$, $-CH=CH-$, or

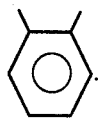

$R_{16}$ is lower alkyl, benzyl, or phenethyl.

$R_{17}$ is hydrogen, lower alkyl, benzyl or phenethyl.

$R_{18}$ is hydrogen, lower alkyl, cycloalkyl, phenyl or

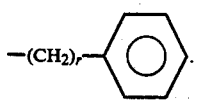

$R_{19}$ is hydrogen, lower alkyl,

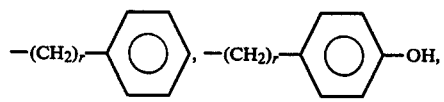

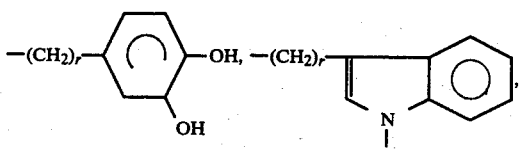

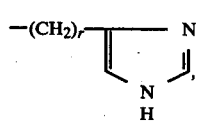

$-(CH_2)_r-NH_2$, $-(CH_2)_r-SH$, $-(CH_2)_r-S-$lower alkyl,

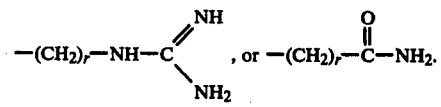

r is an integer from 1 to 4.

DETAILED DESCRIPTION OF THE INVENTION

This invention in its broadest aspects relates to the amino and substituted amino phosphinylalkanoyl compounds of formula I above, to compositions containing such compounds and to the method of using such compounds as anti-hypertensive agents, and to intermediates useful in preparing such compounds.

The term lower alkyl used in defining various symbols refers to straight or branched chain hydrocarbon radicals having up to ten carbons, for example, methyl, ethyl, propyl, isopropyl, butyl, isobutyl, t-butyl, pentyl, isopentyl, etc. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term lower alkenyl refers to straight or branched chain hydrocarbon radicals of 2 to 7 carbons, perferably 2 to 5 carbons, having at least one double bond, for example ethenyl, propenyl, 2-butenyl, etc.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term amino substituted lower alkyl refers to such lower alkyl groups described above in which one or more hydrogens have been replaced by an amino group such as aminomethyl, 1-aminoethyl, 2-aminoethyl, etc.

The symbols

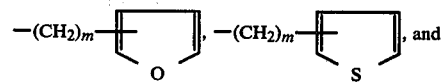

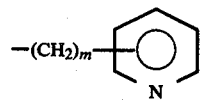

represented that the alkylene bridge is attached to an available carbon atom.

The compounds of formula I are prepared according to the following procedures. An acid or its activated form of formula II wherein $R_1$ is hydrogen, lower alkyl, benzyl, or benzhydryl

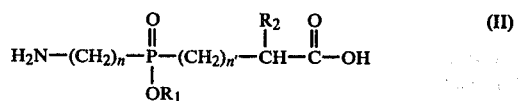

is reacted with an acid chloride, such as

 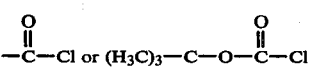

so as to protect the N atom to form a protected acid compound of the formula (III)

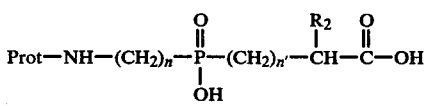

where Prot represents a protecting group, which is coupled with an imino acid or ester of the formula

HX                                                 (IIIA)

to form

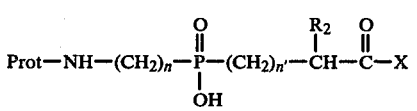

The term activated form refers to the conversion of the acid to a mixed anhydride, symmetrical anhydride, acid chloride, or activated ester, see Methoden der Organischen Chemie (Houben-Weyl), Vol. XV, part II, page 1 et seq. (1974) for a review of the methods of acylation. Preferably, the reaction is performed in the presence of a coupling agent such as 1,1-carbonyldiimidazole or dicyclohexylcarbodiimide.

Deprotection of the resulting product (IV) for example, by treating with hydrogen gas in the presence of a palladium on carbon catalyst when Prot is benzyloxy carbonyl yields the product (I).

Similarly, the products of formula I wherein either or both of $R_1$ and $R_6$ are lower alkyl, benzyl, or benzhydryl can be hydrogenated as described above or chemically treated such as with trifluoroacetic acid and anisole to yield the products of formula I wherein $R_1$ and $R_6$ are hydrogen.

The ester products of formula I wherein $R_6$ is

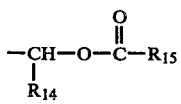

may be obtained by employing the imino acid of formula IIIA in the coupling reaction with the ester group already in place. Such ester starting materials can be prepared by treating the imino acid with an acid chloride such as

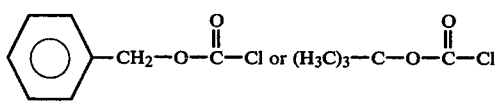

so as to protect the N-atom. The protected imino acid is then reacted in the presence of base with a compound of the formula

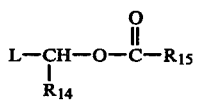

wherein L is a leaving group such as chlorine, bromine, tolylsulfonyl, etc., followed by removal of the N-protecting group such as by treatment with acid or hydrogenation.

The ester products of formula I wherein $R_6$ is

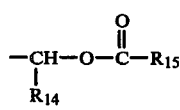

can also be obtained by treating the product of formula I wherein $R_6$ is hydrogen with a molar equivalent of the compound of formula IV. The diester products wherein $R_1$ and $R_6$ are the same and are

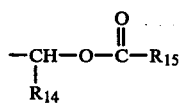

can be obtained by treating the product of formula I wherein $R_1$ and $R_6$ are both hydrogen with two or more equivalents of the compound of formula V.

The ester products of formula I wherein $R_1$ is

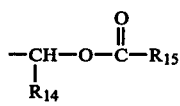

can be obtained by treating the product of formula I wherein $R_1$ is hydrogen and $R_6$ is t-butyl, benzyl or benzhydryl with the compound of formula V in the presence of base. Removal of the $R_6$ ester group such as by hydrogenation yields the products of formula I wherein $R_1$ is

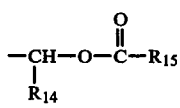

and $R_6$ is hydrogen.

The products of formula I wherein $R_1$ is alkyl or benzyl may be prepared by reacting the product of formula I wherein $R_1$ is hydrogen with an alkylating agent, such as alkyl halide or benzyl halide in the presence of a base. The products of formula I wherein $R_1$ is benzhydryl may be obtained by reacting the product of formula I where $R_1$ is H with diphenyldiazomethane.

The products of formula I wherein $R_3$ is amino may be obtained by reducing the corresponding products of formula I wherein $R_3$ is azido.

The products of formula I wherein $R_3$ is the substituted amino group,

may be obtained by treating the corresponding 4-keto product of formula I with the amine,

in the presence of hydrogen and catalyst or in the presence of sodium cyanotrihydridoborate.

Compounds of formula II may be prepared by reacting a phthamidoalkyl bromide of the structure

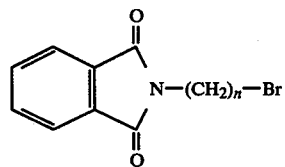

VI with a phosphonous diester of the formula

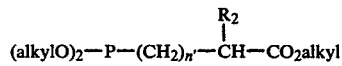

VII to form the phthamido-diester VIII

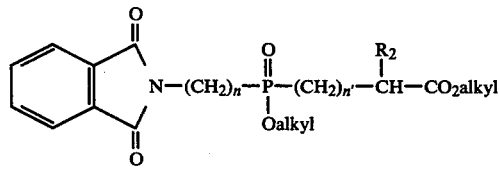

VIII which is then treated with acid to form the formula II compounds.

The phthamidoalkyl bromide of structure VI is obtained by reacting phthalic anhydride with an aminoalkanol of the structure

 VIIIA followed by treatment with PBr₃.

The phosphonous diester VII is prepared by reacting methyltributylstannylacetate, a chlorodialkyl phosphite and a free radical initiator, such as azobisisobutyronitrile (AIBN) in the presence of an aromatic solvent such as benzene.

The various imino acids and esters of formula IV are described in the literature and in the various patents and pending U.S. applications referred to above. Various substituted prolines are disclosed by Mauger et al., Chem. Review, Vol. 66, p. 47–86 (1966). When the imino acid is known, it can be readily converted to the ester by conventional means. For example, the esters where R₆ is t-butyl can be obtained by treating the corresponding N-carbobenzyloxyimino acid with isobutylene under acidic conditions and then removing the N-carbobenzyloxy protecting group by catalytic hydrogenation and the esters wherein R₆ is benzyl can be obtained by treating the imino acid with benzyl alcohol and thionyl chloride.

As disclosed by Krapcho in U.S. Ser. No. 164,985, the substituted prolines wherein R₃ is

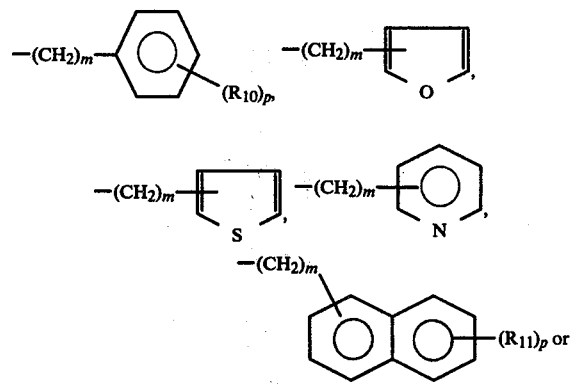

or —(CH₂)$_m$-cycloalkyl are prepared by reacting a 4-keto proline of the formula

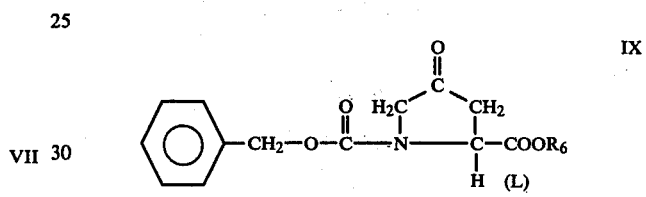

IX with a solution of the Grignard or lithium reagent

R₃-Mg-halo or R₃-Li  (X)

wherein R₃ is as defined above and halo is Br or Cl to yield

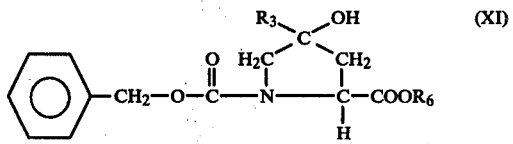

(XI)

This compound is treated with a dehydrating agent such as p-toluenesulfonic acid, sulfuric acid, potassium bisulfate, or trifluoroacetic acid to yield the 3,4-dehydro-4-substituted proline of the formula

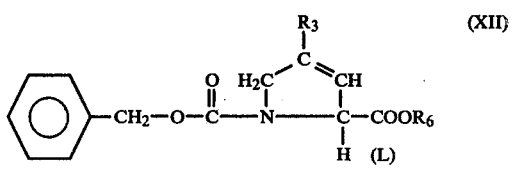

(XII)

Removal of the N-benzyloxycarbonyl protecting group and hydrogenation of the compound of formula XII yields the desired starting materials. The substituted proline wherein R₃ is cyclohexyl can be prepared by further hydrogenation of the 4-phenyl proline compound.

Preferred compounds of this invention with respect to the imino acid or ester part of the structure of formula I are those wherein:

R18 is hydrogen, methyl, phenyl, cyclopentyl, cyclohexyl or benzyl.

R19 is hydrogen, lower alkyl of 1 to 4 carbons,

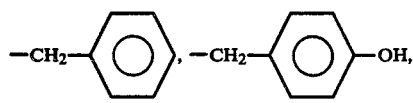

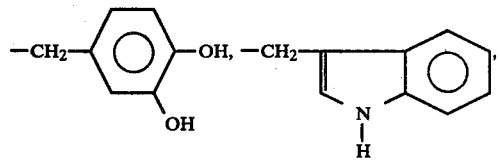

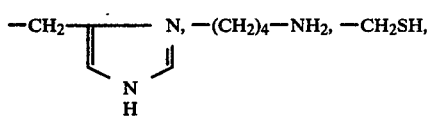

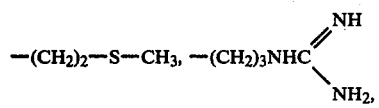

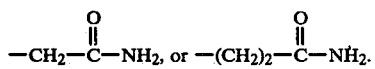

R6 is hydrogen or

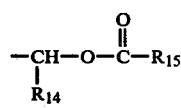

wherein
R14 is hydrogen, methyl or cycloalkyl, such as cyclohexyl, and R15 is straight or branched chain lower alkyl of 1 to 4 carbons or phenyl.

R3 is amino.
R3 is hydrogen.
R3 is hydroxy.
R3 is chloro or fluoro.
R3 is lower alkyl of 1 to 4 carbons or cyclohexyl.
R3 is —O—lower alkyl wherein lower alkyl is straight or branched chain of 1 to 4 carbons.
R3 is

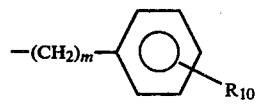

wherein m is zero, one or two, and R10 is hydrogen, methyl, methoxy, methylthio, chloro, bromo, fluoro, or hydroxy.

R3 is

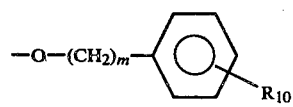

wherein m is zero, one or two, and R10 is hydrogen, methyl, methoxy, methylthio, chloro, bromo, fluoro, or hydroxy.

R3 is —S—lower alkyl wherein lower alkyl is straight or branched chain of 1 to 4 carbons.
R3 is

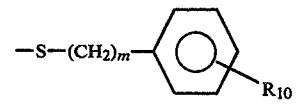

wherein m is zero, one or two, and R10 is hydrogen, methyl, methoxy, methylthio, chloro, bromo, fluoro, or hydroxy.

R4 is —O—lower alkyl wherein lower alkyl is straight or branched chain of 1 to 4 carbons.
R4 is

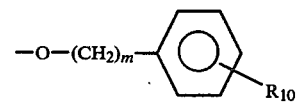

wherein m is zero, one or two, and R10 is hydrogen, methyl, methoxy, methylthio, chloro, bromo, fluoro, or hydroxy.

R4 is —S—lower alkyl wherein lower alkyl is straight or branched chain of 1 to 4 carbons.
R4 is

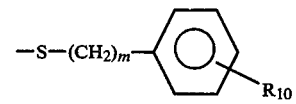

wherein m is zero, one or two, and R10 is hydrogen, methyl, methoxy, methylthio, chloro, bromo, fluoro, or hydroxy.

R5 is phenyl, 2-hydroxyphenyl, or 4-hydroxyphenyl.
Both R7 groups are independently selected from fluoro or chloro.
Both R7 groups are —Y—R13 wherein Y is O or S, R13 is straight or branched chain alkyl of 1 to 4 carbons or the R13 groups join to complete an unsubstituted 5- or 6-membered ring or said ring in which one or more of the carbons has a methyl or dimethyl substitutent.
R8, R8', R9 and R9' are all hydrogen, or R8 is phenyl, 2-hydroxyphenyl or 4-hydroxyphenyl and R8', and R9 and R9' are hydrogen.

Most preferred compounds of this invention with respect to the imino acid or ester part of the structure of formula I are those wherein:
X is

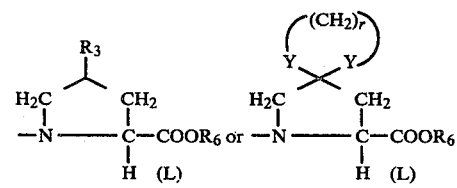

R6 is hydrogen or

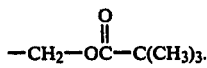

R₃ is hydrogen.
R₃ is cyclohexyl.
R₃ is lower alkoxy of 1 to 4 carbons.
R₃ is

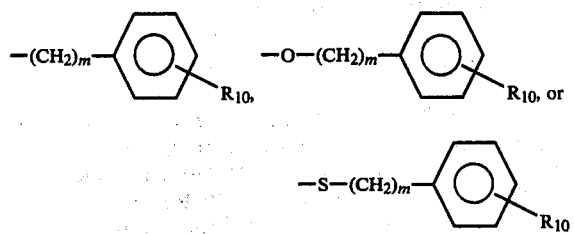

wherein m is zero, one, or two and Rhd 10 is hydrogen, methyl, methoxy, methylthio, Cl, Br, F or hydroxy.

Y is oxygen or sulfur and r is two or three, especially wherein Y is sulfur and r is two.

Preferred compounds of this invention with respect to the phosphinylalkanoyl sidechain of the structure of formula I are those wherein:

$R_1$ is hydrogen or

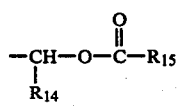

wherein $R_{14}$ is hydrogen or methyl and $R_{15}$ is straight or branched chain lower alkyl of 1 to 4 carbons or phenyl, especially hydrogen or

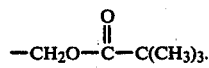

R₂ is hydrogen.
n is 4 to 7.
n' is zero.

The compounds of this invention wherein at least one of $R_1$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product. The salts are formed using conventional techniques.

As shown above, the imino acid or ester portion of the molecule of the products of formula I is in the L-configuration. Depending upon the definition of $R_2$, one asymmetric center may be present in the phosphinylalkanoyl sidechain. Thus, some of the compounds can accordingly exist in diasteroisomeric forms or in mixtures thereof. The above-described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_3$, $R_4$ and $R_5$ substituent in the starting material of formula IIIA.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus, by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative and represent preferred embodiments of the invention. Temperatures are given in degrees centigrade. AG-50W-X8 refers to a crosslinked polystyrenedivinylbenzene sulfonic acid cation exchange resin. HP-20 refers to a porous crosslinked polystyrene-divinylbenzene polymer resin.

EXAMPLE 1

1-[[[(6-Aminohexyl)hydroxy]phosphinyl]acetyl]-L-proline, dilithium salt

A. 6-Phthalimido-1-bromohexane

Ref. Can. J. Chem., 1060, (1953)

A mixture of crystalline 6-aminohexanol (11.7 g, 0.1 mole) and phthalic anhydride (14.8 g, 0.1 mole) was heated to 170° C. for 1.5 hours in an argon atmosphere. The evolved $H_2O$ was then removed with heat and argon flow. The reaction mixture was cooled to 100° C. and $PBr_3$ (7.2 ml, 0.086 mole) was added in portions (via gas tight syringe) to the reaction mixture. A vigorous reaction occured with each addition. After addition was complete the reaction mixture was heated at 100° C. for an additional 30 minutes. The cooled reaction mixture was diluted with ethanol (20 ml) then poured over $H_2O$-/ice and refrigerated overnight. A yellow solid was filtered and washed several times with cold $H_2O$ until the filtrate was slightly acidic. The crude solid was recrystallized from ethanol to give the title compound (21.0 g, 67.7 mmole, 68% yield) as a pale yellow solid, m.p. 54°-55° C.

TLC(1:1 hexane/EtOAc) major spot $R_f=0.8$.

Analysis calcd for $C_{14}H_{16}NO_2Br$: C, 54.21; N, 4.51; H, 5.20; Br, 25.76 Found: C, 54.31; N, 4.58; H, 5.24; Br, 25.59

B. Carbomethoxymethyldichlorophosphine

A mixture of methyltributylstannylacetate (87.0 g, 0.27 mole), chlorodiethylphosphite (34.1 ml, 0.27 mole), azobisisobutyronitrile (AIBN) (250 mg) and benzene (90 ml) was refluxed under argon for 4 hours. The benzene was distilled off at atmospheric pressure in an argon atmosphere. The resulting liquid was distilled in vacuo to obtain the title compound (18.1 g, 93. 2 mmole, 39% yield) as a clear liquid, b.p. 112° C. (20 mmHg).

C. Methyl[[(6-phthalimidohexyl)ethoxy]phosphinyl]acetate

A mixture of the bromide from Part A (2.0 g, 6.45 mmole) and phosphonous diester from Part B (2.5 g, 12.9 mmole) was heated under argon for 3 hours. The volatiles were removed in vacuo (0.5 mmHg) and the orange residue (4.0 g) was chromatographed on silica (120 g) eluting with EtOAc to give the title compound (1.9 g, 4.8 mmole, 74% yield) as an oil. TLC (EtOAc) major spot $R_f=0.3$.

D. [[(6-Aminohexyl)hydroxy]phosphinyl]acetic acid

The phthamido-diester from Part C (1.90 g, 4.8 mmole) was treated with $HOAc/HCl/H_2O$ (6 ml/6 ml/3 ml) then refluxed under argon for 20 hours. The volatiles were removed in vacuo (rotovap). The residue was taken up in water and extracted with ether. The aqueous phase was passed through an AG50WX8 (H+) (60 ml) column; first washing with $H_2O$ and then 10% pyridine/$H_2O$ to elute the compound. The desired fractions were combined and evaporated to give the title compound (0.80 g, 3.4 mmole, 71% yield) as a white solid.

Electrophoresis: pH 6.5, 2000 V, 45 minutes, major spot +3.8 cm, visualized with carboxyl reagent +Δ, trace impurity −1.0 cm, visualized with ninhydrin +Δ, m.p. 236°-238° C.

Analysis Calcd for $C_8H_{18}NO_4P$: C, 43.05; H, 8.13; N, 6.27; P, 13.87 Found: C, 42.69; H, 8.41; N, 6.41; P, 13.8

E. [[6-Benzyloxycarbonylaminohexyl)hydroxy]phosphinyl]acetic acid

A suspension of the amino diacid from Part D (0.75 g, 3.4 mmole) in dry $CH_3CN$ (7 ml) in an argon atmosphere at 25° C. was treated with bis-trimethylsilyltrifluoroacetamide (3.5 g, 13.6 mmole). A slight exotherm occured and after 20 minutes the mixture became homogeneous. After an additional 40 minutes, benzyl chloroformate (0.9 g, 5.1 mmole) was added in portions. After 16 hours, the reaction mixture was quenched with $H_2O$ (3 ml). The mixture was taken into saturated $NaHCO_3$, washed with ether (2x), and acidified with concentrated HCl. The resulting oil was extracted into EtOAc (2x), washed with brine, dried ($MgSO_4$), and evaporated to obtain a white solid (1.1 g). the crude solid was recrystallized from EtOAc (2x) to give the title compound (0.85 g, 2.4 mmole, 71% yield) as a white solid.

TLC (7/2/1 isopropanol/conc. $NH_4OH/H_2O$) single spot $R_f=0.5$, m.p. 95°-96° C.

Analysis Calcd for $C_{16}H_{24}NO_6P$: C, 53.78; H, 6.77; N, 3.92; P, 8.7 Found: C, 53.86; H, 6.80; N, 3.77; P, 8.3

F. 1-[[[(6-Benzyloxycarbonylaminohexyl)hydroxy]phosphinyl]acetyl]-L-proline, benzyl ester A mixture of the protected amino diacid from Part E (780 mg, 2.18 mmole), THF (5 ml), and 1,1-carbonyldiimidazole (350 mg, 2.18 mmole) was stirred at 0° C. for 45 minutes under argon. The reaction mixture was then treated with $NEt_3$ (0.6 ml, 4.4 mmole) and L-proline, benzyl ester, hydrochloride (630 mg, 2.6 mmole), the ice-bath removed, and the resulting solution stirred for 16 hours. The reaction mixture was diluted with EtOAc then washed with 5% $KHSO_4$, 5% $Na_2HPO_4$ (2x), brine, dried ($MgSO_4$) and evaporated. The residue (1.1 g) was chromatographed on silica (90 g) eluting with $CH_2Cl_2/CH_3OH/HOAc$ (100/5/5). After evaporation and azeotropic removal of HOAc with toluene, the title compound (1.0 g, 1.84 mmole, 84% yield) was obtained as colorless glass.

TLC: (isopropanol/conc. $NH_4OH/H_2O$ 7:2:1) single spot $R_f=0.7$.

G. 1-[[[(6-Aminohexyl)hydroxy]phosphinyl]acetyl]-L-proline, dilithium salt

A mixture of the benzyl ester from Part F (1.0 g 1.84 mmole), $CH_3OH$ (70 ml), and 10% Pd/C (1.1 g) was hydrogenated on the Parr apparatus at 50 psi for 3 hours. The catalyst was removed by filtration through a Celite bed and the $CH_3OH$ stripped. The crude oil (0.50 g) was taken up in $H_2O$ and applied to an AG50WX8 (H+) (10 ml) column eluting first with $H_2O$ then with 10% pyridine/$H_2O$. The desired fractions were combined, the solvent stripped, and the residual pyridine azeotropically removed with toluene. The residue was taken up in $H_2O$, filtered (millipore), and lyophilized to give a glassy solid (350 mg). The solid was passed through an AG50WX8 (Li+) (10 ml) column eluting with H₂O. The desired fractions were combined, taken to small volume, and chromatographed on an HP-20 (200 ml) column eluting with a linear gradient H₂O/CH₃CN (0→90%). The desired fractions were combined, stripped to dryness, taken into H₂O, filtered (millipore), and lyophilized to give the title product (90 mg, 0.28 mmole, 15% yield) as a glassy solid.

TLC: (7:2:1 isopropanol/conc. NH₄OH/H₂O) single spot $R_f$=0.3.

Analysis calcd for $C_{13}H_{23}N_2O_5PLi$ 1.3 mmoles H₂O: C, 43.91; H, 7.25; N, 7.88; P, 8.7 Found: C, 43.93; H, 7.25; N, 7.88; P, 8.7

EXAMPLES 2-84

Following the procedure of Example 1 but substituting for 6-aminohexanol, the aminoalkanol shown in Col. I, and substituting the phosphonous diester shown in Col. II and the imino acid shown in Col. III, one obtains the product shown in Col. IV. Hydrogenation of the product of Col. IV in examples where $R_6$=benzyl or treatment of the product with acid in examples where $R_6$=t-butyl yields the corresponding acid product ($R_6$ is H). Passage of the acid through an Li column yields the corresponding dilithium salt. In examples 58-63, the $R_6$ group is not removed.

Reaction of the product of Col. IV with an alkylating agent, such as alkyl halide, benzyl halide or acyloxyalkyl halide yields the corresponding product wherein $R_1$ is alkyl, benzyl or acyloxyalkyl, respectively. Reaction of the product of Col. IV with diphenyldiazomethane yields the product wherein $R_1$ is benzhydryl.

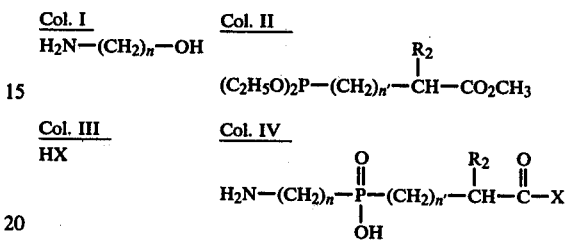

| Ex. | n | n' | R₂ | X |
|---|---|---|---|---|
| 2. | 4 | 1 | —H | 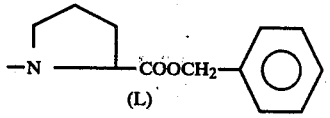 |
| 3. | 5 | 0 | —CH₃ | 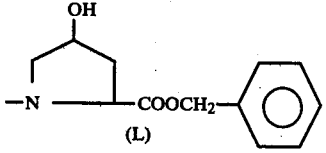 |
| 4. | 4 | 0 | —CH₂CCl₃ | 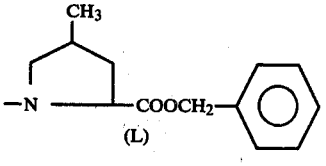 |
| 5. | 5 | 0 | 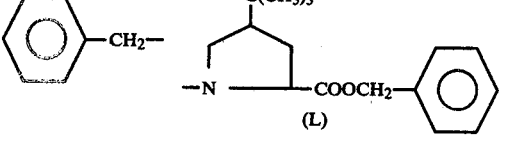 | 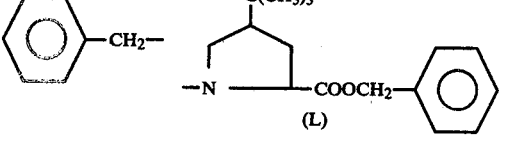 |
| 6. | 6 | 1 | —H | 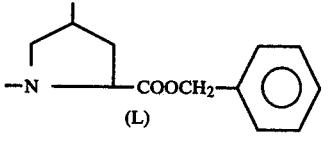 |
| 7. | 6 | 0 | —H | 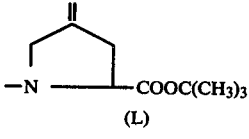 |

-continued
| Ex. | n | n' | R₂ | X |
|---|---|---|---|---|
| 8. | 5 | 0 | —H | 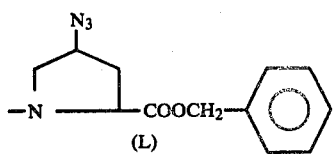 |
| 9. | 4 | 0 | —CH₃ | 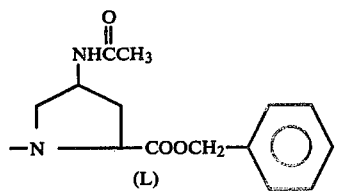 |
| 10. | 5 | 1 | —H | 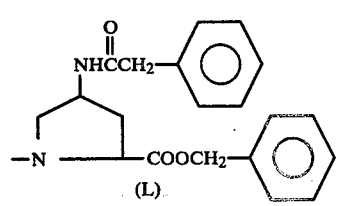 |
| 11. | 6 | 0 | —H | 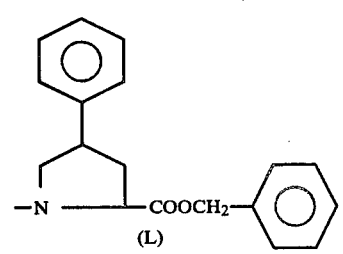 |
| 12. | 5 | 0 | —H | 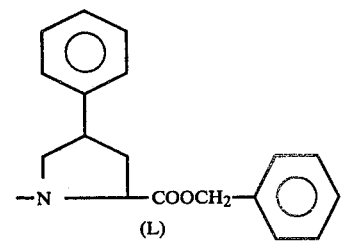 |
| 13. | 6 | 0 | —H | 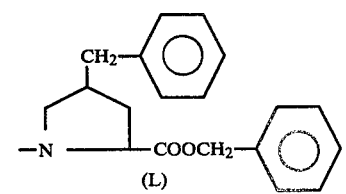 |
| 14. | 7 | 0 | —H | 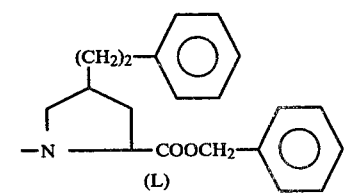 |

-continued
| Ex. | n | n' | R₂ | X |
|---|---|---|---|---|
| 15. | 4 | 0 | —H | 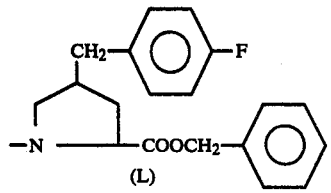 |
| 16. | 5 | 1 | —H | 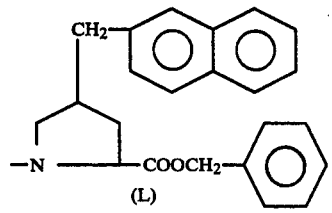 |
| 17. | 6 | 0 | —H | 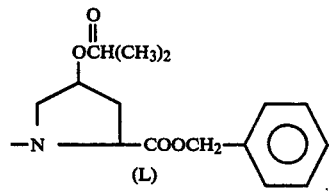 |
| 18. | 6 | 1 | —H | 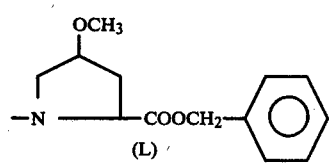 |
| 19. | 5 | 0 | —CH₃ | 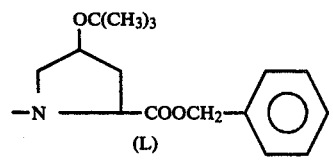 |
| 20. | 4 | 0 | —H | 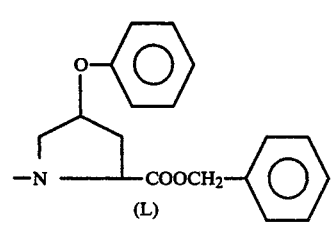 |
| 21. | 6 | 0 | —H | 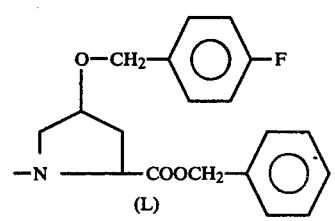 |

-continued
| Ex. | n | n' | R₂ | X |
|---|---|---|---|---|
| 22. | 6 | 0 | —H | 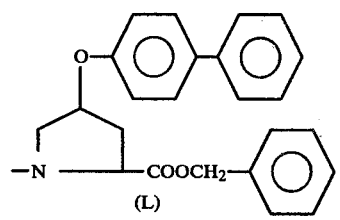 (L) |
| 23. | 6 | 1 | —H | 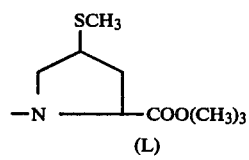 (L) |
| 24. | 4 | 0 | —CH₃ | 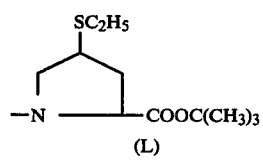 (L) |
| 25. | 5 | 0 | —H | 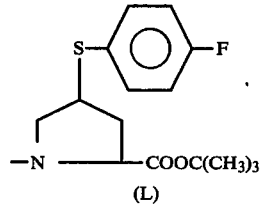 (L) |
| 26. | 6 | 0 | —H | 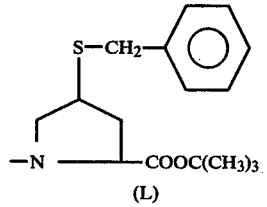 (L) |
| 27. | 8 | 0 | —H | 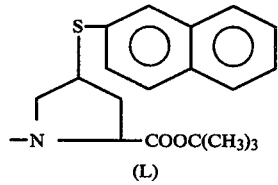 (L) |
| 28. | 5 | 1 | —CH₃ | 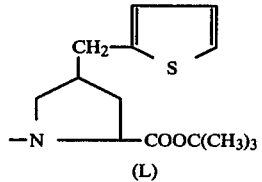 (L) |
| 29. | 6 | 0 | —H | 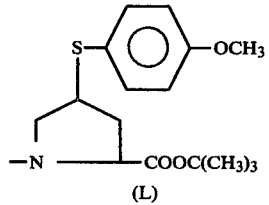 (L) |

-continued
| Ex. | n | n' | R₂ | X |
|---|---|---|---|---|
| 30. | 6 | 0 | —H | 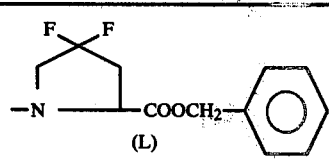 (L) |
| 31. | 5 | 0 | —H | 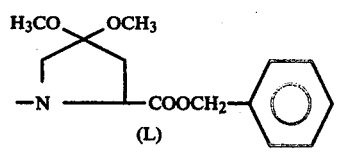 (L) |
| 32. | 6 | 0 | —H | 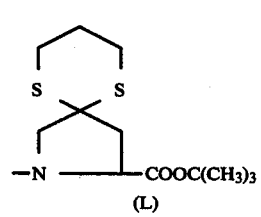 (L) |
| 33. | 5 | 0 | —H | 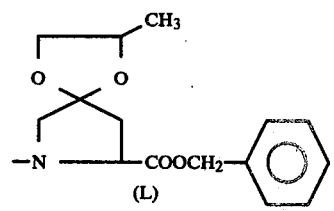 (L) |
| 34. | 6 | 0 | —H | 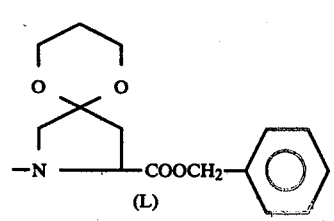 (L) |
| 35. | 7 | 0 | —H | 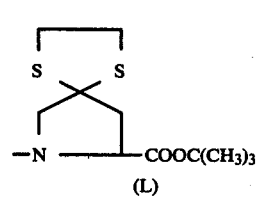 (L) |
| 36. | 5 | 0 | —CH₃ | 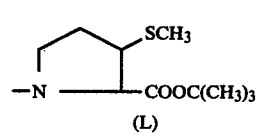 (L) |
| 37. | 5 | 0 | —H | 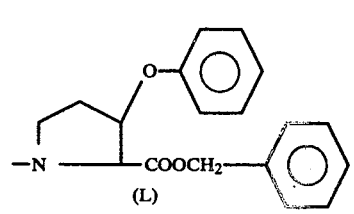 (L) |

-continued

| Ex. | n | n' | R₂ | X |
|---|---|---|---|---|
| 38. | 8 | 0 | —H | pyrrolidine with 2-substituent —O—CH₂—C₆H₄—OCH₃ (para) and 2-COOCH₂C₆H₅ (L) |
| 39. | 7 | 1 | —H | pyrrolidine with 3-substituent —S—C₆H₄—F (para) and 2-COOC(CH₃)₃ (L) |
| 40. | 6 | 0 | —H | pyrrolidine with 2-substituent —S—CH₂—C₆H₅ and 2-COOC(CH₃)₃ (L) |
| 41. | 5 | 0 | —H | 2,3-dihydro-pyrrole with 2-COOCH₂C₆H₅ (L) |
| 42. | 6 | 0 | —H | pyrrolidine with 2-COOCH₂C₆H₅ (L) |
| 43. | 6 | 0 | —H | pyrrolidine with 2-COOCH₂C₆H₅ (L) |
| 44. | 6 | 1 | —H | piperidine with 4-S—C₆H₅ and 2-COOC(CH₃)₃ (L) |
| 45. | 5 | 0 | —CH₃ | 3-oxo-pyrrolidine with 2-COOCH₂C₆H₅ (L) |
| 46. | 5 | 0 | —H | pyrrolidine with 5-phenyl and 2-COOCH₂C₆H₅ (L) |

-continued
| Ex. | n | n' | R₂ | X |
|---|---|---|---|---|
| 47. | 6 | 1 | —H | 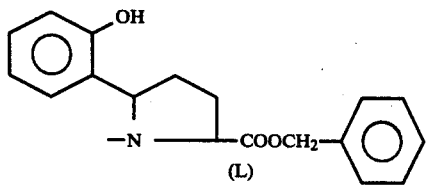 (L) |
| 48. | 6 | 0 | —CH₃ | 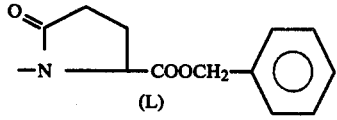 (L) |
| 49. | 5 | 0 | —H | 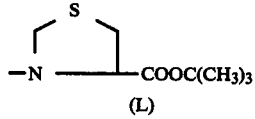 (L) |
| 50. | 5 | 0 | —H | 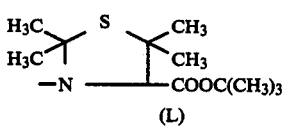 (L) |
| 51. | 6 | 0 | —H | 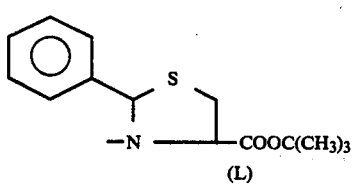 (L) |
| 52. | 5 | 0 | —H | 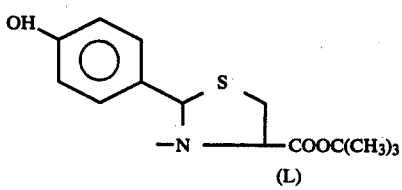 (L) |
| 53. | 5 | 0 | —H | 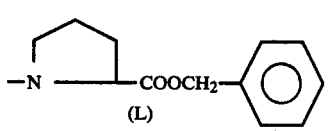 (L) |
| 54. | 4 | 0 | —H | 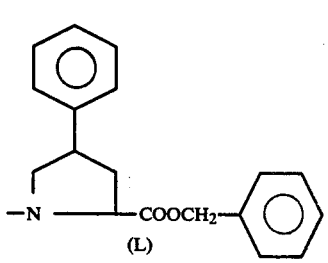 (L) |
| 55. | 6 | 0 | —H | 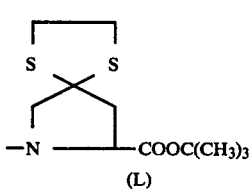 (L) |

-continued
| Ex. | n | n' | R₂ | X |
|---|---|---|---|---|
| 56. | 5 | 0 | —H | 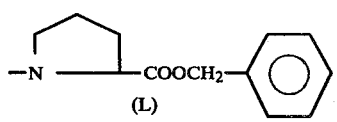 |
| 57. | 8 | 0 | —H | 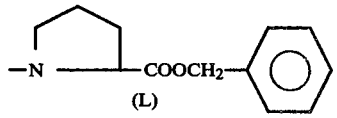 |
| 58. | 4 | 0 | —H | 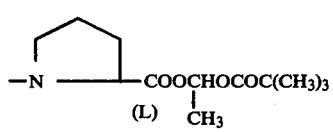 |
| 59. | 6 | 0 | —H | 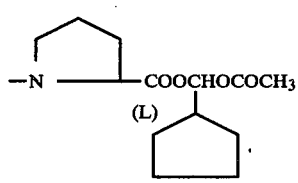 |
| 60. | 8 | 0 | —CH₃ | 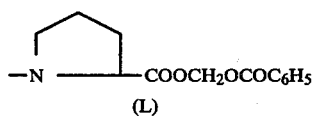 |
| 61. | 6 | 0 | —H | 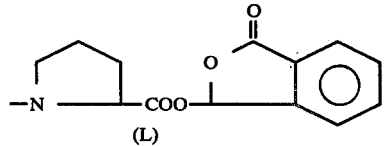 |
| 62. | 5 | 1 | —H | 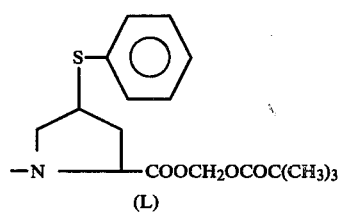 |
| 63. | 6 | 0 | —H | 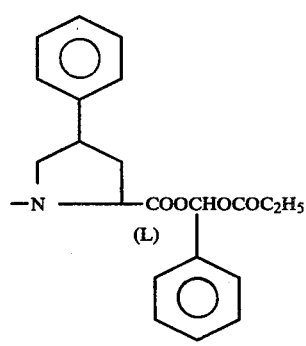 |

-continued
| Ex. | n | n' | R₂ | X |
|---|---|---|---|---|
| 64. | 6 | 0 | —CH₃ | 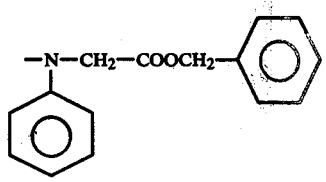 |
| 65. | 8 | 1 | —CH₃ | 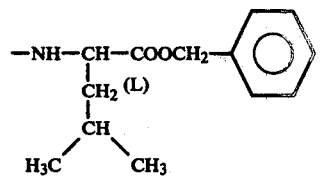 |
| 66. | 5 | 0 | —CH₃ | 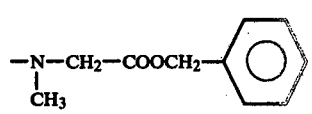 |
| 67. | 4 | 1 | —CH₃ | 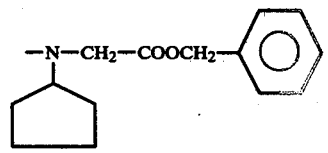 |
| 68. | 4 | 0 | —CH₃ | 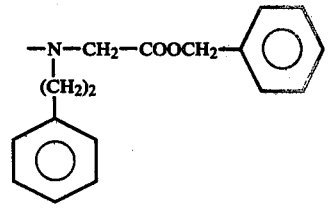 |
| 69. | 4 | 1 | —H | 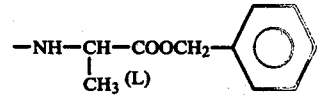 |
| 70. | 6 | 0 | —CH₃ | 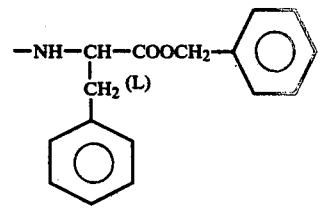 |
| 71. | 7 | 1 | —CH₃ | 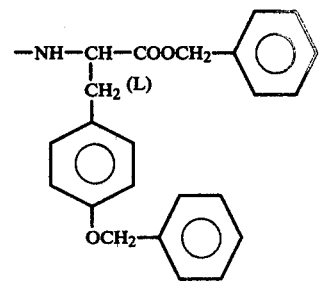 |

-continued

| Ex. | n | n' | R₂ | X |
|---|---|---|---|---|
| 72. | 5 | 0 | —CH₃ | -N(C₆H₅)—CH₂—COOCH₂—C₆H₅ |
| 73. | 6 | 1 | —CH₃ | —NH—CH(CH₂-indol-3-yl)—COOCH₂—C₆H₅ (L) |
| 74. | 7 | 0 | —CH₃ | —NH—CH(CH₂-[1-benzylimidazol-4-yl])—COOCH₂—C₆H₁₁ (L) |
| 75. | 8 | 1 | —CH₃ | —NH—CH[(CH₂)₄—NHCOCH₂C₆H₅]—COOCH₂—C₆H₅ (L) |
| 76. | 4 | 0 | —CH₃ | —NH—CH[CH₂—SC(C₆H₅)₃]—COOC(CH₃)₃ (L) |
| 77. | 5 | 1 | —CH₃ | —NH—CH[(CH₂)₂—S—CH₃]—COOC(CH₃)₃ (L) |
| 78. | 6 | 0 | —CH₃ | —NH—CH[(CH₂)₃—NHC(=NH)NH—NO₂]—COOCH₂—C₆H₅ (L) |
| 79. | 7 | 1 | —CH₃ | —NH—CH[CH₂—C(=O)NH₂]—COOCH₂—C₆H₅ (L) |

-continued

| Ex. | n | n' | R₂ | X |
|---|---|---|---|---|
| 80. | 8 | 0 | —CH₃ | 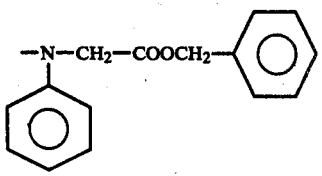 |
| 81. | 8 | 0 | H | 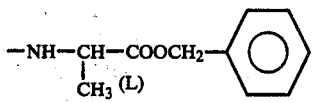 |
| 82. | 6 | 1 | CH₃ | 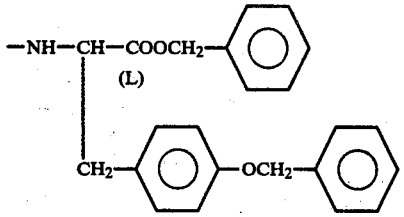 |
| 83. | 4 | 1 | C₂H₅ | 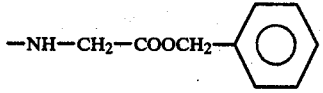 |
| 84. | 5 | 0 | H | 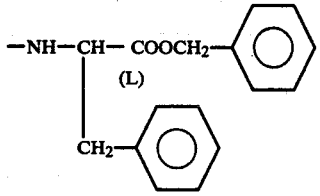 |

Reduction of the product of Example 8 yields the corresponding 4-amino product. Similarly, the 4-keto product of Example 7 can be reacted to yield various 4-substituted amino products.

EXAMPLE 85

1000 Tablets each containing the following ingredients:

| | |
|---|---|
| 1-[[[1-(6-Aminohexyl)hydroxy]phosphinyl]acetyl]-L-proline, dilithium salt | 100 mg |
| Corn starch | 50 mg |
| Gelatin | 7.5 mg |
| Avicel (microcrystalline cellulose) | 25 mg |
| Magnesium stearate | 2.5 mg |
| | 185 mg | are prepared from sufficient bulk quantities by mixing the 1-[[[1-(6-aminohexyl)hydroxy]phosphinyl]acetyl]-L-proline, dilithium salt and corn starch with an aqueous solution of the gelatin. The mixture is dried and ground to a fine powder. The Avicel and then the magnesium stearate are admixed with granulation. This mixture is then compressed in a tablet to form 1000 tablets each containing 100 mg of active ingredient.

In a similar manner, tablets containing 100 mg of the product of any of Examples 2 to 84 can be prepared.

EXAMPLE 86

1000 Tablets each containing the following ingredients:

| | |
|---|---|
| 1-[[[-(6-Aminohexyl)hydroxy]phosphinyl]acetyl]-L-proline, dilithium salt | 50 mg |
| Lactose | 25 mg |
| Avicel | 38 mg |
| Corn starch | 15 mg |
| Magnesium stearate | 2 mg |
| | 130 mg | are prepared from sufficient bulk quantities by mixing the 1-[[[1-(6-aminohexyl)hydroxy]phosphinyl]acetyl]-L-proline, dilithium salt, lactose, and Avicel and then blending with the corn starch. Magnesium stearate is added and the dry mixture is compressed in a tablet press to form 1000 tablets each containing 50 mg of active ingredient. The tablets are coated with a solution of Methocel E 15 (methyl cellulose) including as a color a lake containing yellow #6.

In a similar manner, tablets containing 50 mg of the product of any of Examples 2 to 84 can be prepared.

EXAMPLE 87

Two piece #1 gelatin capsules each containing 100 mg of 1-[[[1-(6-aminohexyl)hydroxy]phosphinyl]acetyl]-L-proline, dilithium salt are filled with a mixture of the following ingredients:

1-[[[1-(6-aminohexyl)hydroxy]phosphinyl]acetyl]-L-proline, dilithium salt: 100 mg
Magnesium stearate: 7 mg
Lactose: 193 mg In a similar manner, capsules containing 100 mg of the product of any of Examples 2 to 84 can be prepared.

EXAMPLE 88

An injectable solution is prepared as follows:

1-[[[1-(6-Aminohexyl)hydroxy]phosphinyl]acetyl]-L-proline, dilithium salt: 500 g
Methyl paraben: 5 g
Propyl paraben: 1 g
Sodium chloride: 25 g
Water for injection: 5 l.

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml of solution in a concentration of 100 mg of active ingredient per ml of solution for injection.

In a similar manner, an injectable solution containing 100 mg of active ingredient per ml of solution can be prepared for the product of any of Examples 2 to 84.

EXAMPLE 89

1000 Tablets each containing the following ingredients:

| | |
|---|---|
| 1-[[[-(6-Aminohexyl)hydroxy]-phosphinyl]acetyl]-L-proline, dilithium salt | 100 mg |
| Avicel | 100 mg |
| Hydrochlorothiazide | 12.5 mg |
| Lactose | 113 mg |
| Corn starch | 17.5 mg |
| Stearic acid | 7 mg |
| | 350 mg | are prepared from sufficient bulk quantities by slugging the 1-[[[1-(6-aminohexyl)hydroxy]phosphinyl]acetyl]-L-proline, dilithium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg capsule shaped tablets in a tablet press. The tablets are scored for dividing in half.

In a similar manner, tablets can be prepared containing 100 mg of the product of any of Example 2 to 84.

EXAMPLE 90

1-[[[(6-Benzyloxycarbonylaminohexyl)-(2,2-dimethyl-1-oxopropoxy)methoxy]phosphinyl]acetyl]-L-proline

A.

1-[[[(6-Benzyloxycarbonylaminohexyl)-(2,2-dimethyl-1-oxopropoxy)methoxy]phosphinyl]acetyl]-L-proline, benzyl ester A solution of the benzyl ester from Example 1, Part F (0.64 g, 1.5 mmole), triethylamine (0.42 ml, 3.0 mmole) and chloromethyl pivalate (0.45 g, 3.0 mmole) in dry dimethylformamide (5 ml) is stirred at room temperature under argon for 16 hours. The mixture is then partitioned between EtOAc-water. The organic phase is washed successively with 5% $KHSO_4$, saturated $NaHCO_3$ and saturated NaCl, dried over $Na_2SO_4$ and evaporated. The crude product is purified by flash chromatography on silica gel to give the title A compound.

B.

1-[[[(6-Aminohexyl)-(2,2-dimethyl-1-oxopropoxy)methoxy]phosphinyl]acetyl]-L-proline A mixture of the ester from Part A (1.0 g, 1.84 mmole), $CH_3OH$ (50 ml), and 10% Pd/C (0.5 g) is hydrogenated on the Parr apparatus at 50 psi for 3 hours. The catalyst is removed by filtration through a Celite bed and the $CH_3OH$ stripped. The crude product is purified by chromatography on HP-20 eluting with a gradient of water-acetonitrile (0→90% $CH_3CN$). The fractions containing the desired material are combined, evaporated, taken up in water and lyophilized to give the title compound.

EXAMPLES 91–95

Following the procedure of Example 90 but employing the alkylating agent shown in Col. I in place of the chloromethyl pivalate, one obtains the product in Col. II.

| Ex. | Col. I | Col. II |
|---|---|---|
| 91. | BrCH$_2$OC(=O)—CH$_3$ | 1-[[Acetoxymethoxy-(6-aminohexyl)phosphinyl]-acetyl]-L-proline |
| 92. | Cl—CH(CH$_3$)—O—COC$_2$H$_5$ (=O) | 1-[[6-Aminohexyl-1-[(ethoxycarbonyloxy)-ethoxy]phosphinyl]acetyl]-L-proline |
| 93. | Br-substituted oxo-isobenzofuranyl | 1-[[6-Aminohexyl-1-(7-oxo-isobenzofuranyloxy)-phosphinyl]acetyl]-L-proline |
| 94. | ClCH$_2$O—C(=O)—phenyl | 1-[[6-Aminohexyl-(benzoyloxymethoxy)phosphinyl]-acetyl]-L-proline |
| 95. | Cl—CH(CH(CH$_3$)$_2$)—O—C(=O)—C$_2$H$_5$ | 1-[[[6-Aminohexyl-[2-methyl-1-(1-oxopropoxy)]-propoxy]phosphinyl]acetyl]-L-proline |

Similarly, the alkylating agents of Examples 90–95 can be employed with the appropriately protected compounds of Examples 1 to 89 to yield other compounds within the scope of this invention. In the cases where the proline carboxyl group is protected as its phenylmethyl ester rathen than its t-butyl ester, it is removed by hydrogenation in the presence of Pd/C in the final step.

What is claimed is:

1. A compound of the formula

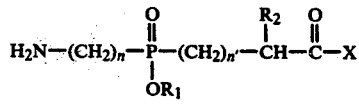

wherein
X is an imino acid of the formula

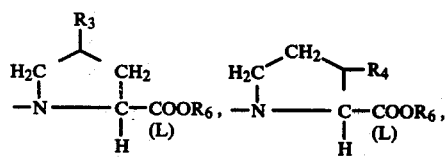

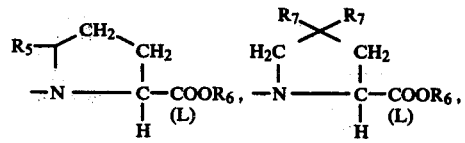

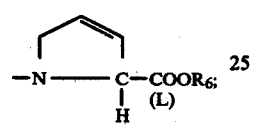

R₃ is hydrogen, lower alkyl, halogen, keto, hydroxy,

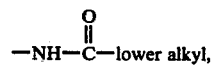

azido, amino,

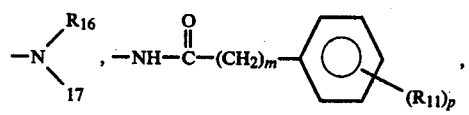

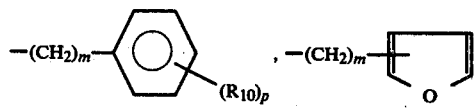

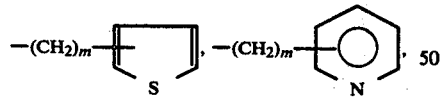

a 1- or 2-naphthyl of the formula

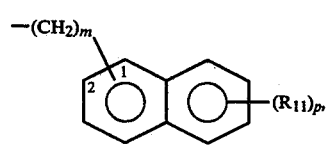

—(CH₂)$_m$-cycloalkyl,

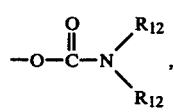

—O—lower alkyl,

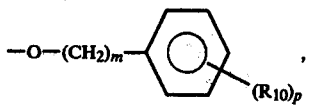

a 1- or 2-naphthyloxy of the formula

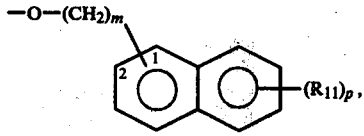

—S—lower alkyl,

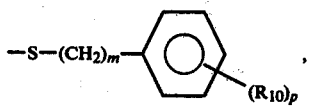

or a 1- or 2-naphthylthio of the formula

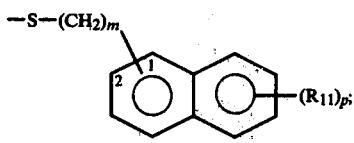

R₄ is keto, halogen,

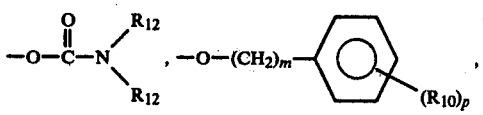

—O—lower alkyl, a 1- or 2-naphthyloxy of the formula

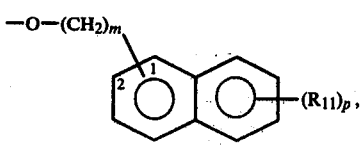

—S—lower alkyl,

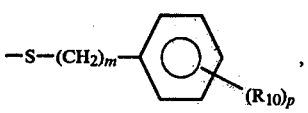

or a 1- or 2-naphthylthio of the formula

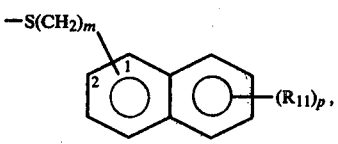

R₅ is keto or

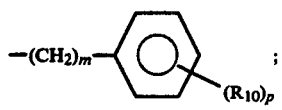

R$_7$ is halogen or —Y—R$_{13}$;

R$_{10}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

R$_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

m is zero, one, two or three;

p is one, two or three provided that p is more than one only if R$_{10}$ or R$_{11}$ is hydrogen, methyl, methoxy, chloro, or fluoro;

R$_{12}$ is hydrogen or lower alkyl of 1 to 4 carbons;

Y is oxygen or sulfur;

R$_{13}$ is lower alkyl of 1 to 4 carbons,

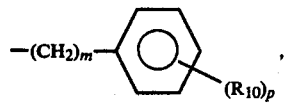

or the R$_{13}$ groups join to complete an unsubstituted 5- or 6-membered ring or said ring in which one or more of the carbons has a lower alkyl of 1 to 4 carbons or a di(lower alkyl of 1 to 4 carbons) substituent;

n is an integer of from 4 to 8;

n' is zero or one;

R$_2$ is hydrogen, lower alkyl, halo substituted lower alkyl, benzyl or phenethyl;

R$_1$ and R$_6$ are independently selected from hydrogen, lower alkyl, benzyl, benzhydryl, or

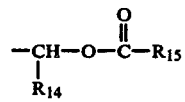

wherein R$_{14}$ is hydrogen, lower alkyl, cycloalkyl or phenyl, and R$_{15}$ is hydrogen, lower alkyl, lower alkoxy, phenyl, or R$_{14}$ and R$_{15}$ taken together are —(CH$_2$)$_2$—, —(CH$_2$)$_3$—, —CH=CH—, or

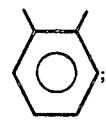

and when either or both of R$_1$ and R$_6$ are hydrogen a basic addition salt or an amino acid addition salt thereof.

2. A compound of claim 1 wherein n is 4 to 7.

3. A compound of claim 2 wherein X is

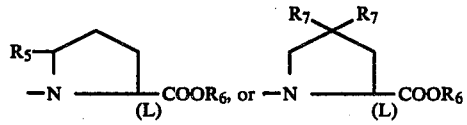

R$_3$ is hydrogen, hydroxy, amino, lower alkyl of 1 to 4 carbons, cyclohexyl, lower alkoxy of 1 to 4 carbons,

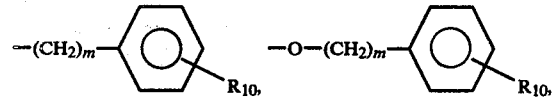

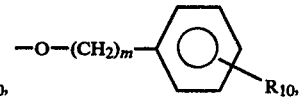

or lower alkylthio of 1 to 4 carbons;

R$_4$ is lower alkoxy of 1 to 4 carbons, lower alkylthio of 1 to 4 carbons,

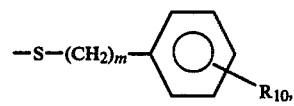

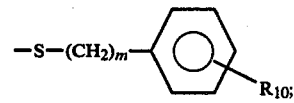

R$_5$ is phenyl, 2-hydroxyphenyl, or 4-hydroxyphenyl;

m is zero, one or two;

R$_{10}$ is hydrogen, methyl, methoxy, methylthio, chloro, bromo, fluoro, or hydroxy;

R$_7$ is fluoro, chloro, or —Y—R$_{13}$;

Y is O or S;

R$_{13}$ is lower alkyl of 1 to 4 carbons or the R$_{13}$ groups join to complete an unsubstituted 5- or 6-membered ring or said ring in which one or more of the available carbon atoms has a methyl or dimethyl substituent;

R$_6$ is hydrogen or

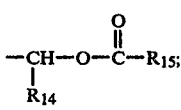

R$_{14}$ is hydrogen, methyl or isopropyl; and

R$_{15}$ is lower alkyl of 1 to 4 carbons or phenyl.

4. A compound of claim 3 wherein X is

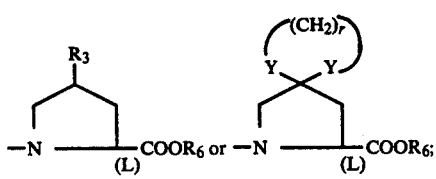

R₃ is hydrogen, cyclohexyl,

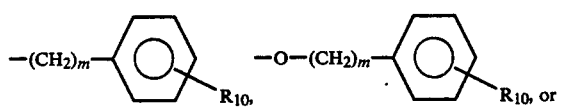

m is zero, one or two;

R₁₀ is hydrogen, methyl, methoxy, methylthio, Cl, Br, F, or hydroxy;

Y is O or S;

r is two or three; and

R₆ is hydrogen or

5. A compound of claim 4 wherein R₁ is hydrogen or alkali metal.

6. The compound of claim 4 wherein

R₁ is hydrogen; and

X is

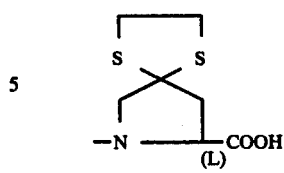

or L-proline.

7. The compound of claim 1 wherein n is 6, R₁ is hydrogen, n' is 0, R₂ is hydrogen and X is L-proline.

8. The lithium salt of the compound of claim 5.

9. The compound of claim 7 wherein R₁ is hydrogen or

10. The compound of claim 1 wherein R₆ is hydrogen or

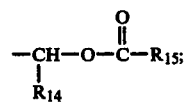

wherein R₁₄ is hydrogen, methyl, cyclopentyl or cyclohexyl and R₁₅ is lower alkyl of 1 to 4 carbons or phenyl.

11. The compound of claim 1 of the formula

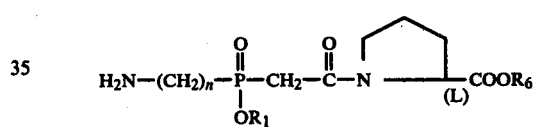

wherein n is 4 to 6; and

R₁ and R₆ are independently selected from the group consisting of lower alkyl, benzyl, and benzhydryl.

12. A pharmaceutical composition useful for treating hypertension comprising a pharmaceutically acceptable carrier and one or more compounds of claim 1 or pharmaceutically acceptable salts thereof.

13. The method of treating hypertension in a mammalian specie comprising administering an effective amount of the composition of claim 12.

* * * * *

UNITED STATES PATENT AND TRADEMARK OFFICE
CERTIFICATE OF CORRECTION

PATENT NO. : 4,444,765
DATED : April 24, 1984
INVENTOR(S) : Donald S. Karanewsky et al.

It is certified that error appears in the above—identified patent and that said Letters Patent is hereby corrected as shown below:

Title page, in the Abstract, first line after the structure, "amino" should read --imino--.
Column 1, line 49, "emzyme" should read --enzyme--.
Column 5, line 55, the first structure should read

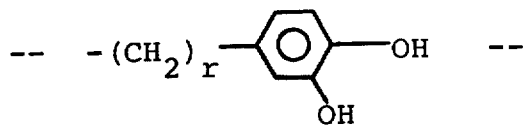

Column 13, line 21, "Rhd 10" should read --$R_{10}$--.

Signed and Sealed this

Sixth Day of November 1984

[SEAL]

Attest:

GERALD J. MOSSINGHOFF

Attesting Officer

Commissioner of Patents and Trademarks